(12) United States Patent
Hossack et al.

(10) Patent No.: US 6,503,202 B1
(45) Date of Patent: Jan. 7, 2003

(54) MEDICAL DIAGNOSTIC ULTRASOUND SYSTEM AND METHOD FOR FLOW ANALYSIS

(75) Inventors: John A. Hossack, Charlottesville, VA (US); Thilaka S. Sumanaweera, San Jose, CA (US); Anming He Cai, San Jose, CA (US); Sandy Napel, Menlo Park, CA (US); David Paik, Palo Alto, CA (US); Brooke Jeffrey, Jr., Los Altos Hills, CA (US)

(73) Assignee: Acuson Corp., Mountain View, CA (US)

( * ) Notice: Subject to any disclaimer, the term of this patent is extended or adjusted under 35 U.S.C. 154(b) by 165 days.

(21) Appl. No.: 09/607,556

(22) Filed: Jun. 29, 2000

(51) Int. Cl.7 ................................................. A61B 8/02
(52) U.S. Cl. ...................................................... 600/454
(58) Field of Search ................................ 600/443–447, 600/454–467; 128/916; 73/625, 626; 367/7, 11, 130; 333/138

(56) References Cited

U.S. PATENT DOCUMENTS

| 5,474,073 A | 12/1995 | Schwartz et al. |
| 5,477,858 A | * 12/1995 | Norris et al. ................ 333/138 |
| 5,623,930 A | 4/1997 | Wright et al. |
| 5,771,896 A | 6/1998 | Sliwa, Jr. et al. |
| 5,876,345 A | 3/1999 | Eaton et al. |
| 5,928,151 A | 7/1999 | Hossack et al. |
| 5,967,987 A | 10/1999 | Sumanaweera et al. |
| 6,014,473 A | 1/2000 | Hossack et al. |
| 6,045,508 A | 4/2000 | Hossack et al. |

OTHER PUBLICATIONS

Paik et al., "Automated Flight Path Planning for Virtual Ends" Medical Physics, May, 1998; 25(5): 629–637.
Scott Unbaugh; "Computer Vision and Image Processing—A Practical Approach . . . ", Prentice Hall PTR, Upper Saddle River, NJ 07458.
Carlo Palombo, MD; Ultrafast Three–Dimensional Ultrasound—Application to Carotid Artery Imaging; pp. 1631–1637.

* cited by examiner

Primary Examiner—Marvin M. Lateef
Assistant Examiner—Ali M. Imam (57) ABSTRACT

Medical diagnostic ultrasound methods and systems for automated flow analysis are provided. Multiple cross-sectional areas along a vessel are determined automatically. A processor locates an abnormality as a function of the multiple cross-sectional areas, such as identifying a cross-sectional area that is a threshold amount less than an average cross-sectional area. The abnormal area is highlighted on the display to assist with medical diagnosis. For the carotid artery, the interior and exterior branches are labeled to assist medical diagnosis. The two branches are automatically identified. The branch associated with additional small branches is identified as the exterior carotid.

33 Claims, 3 Drawing Sheets

MEDICAL DIAGNOSTIC ULTRASOUND SYSTEM AND METHOD FOR FLOW ANALYSIS

BACKGROUND

This invention relates to a medical diagnostic ultrasound system and method for flow analysis. In particular, abnormalities, such as arterial stenosis or constriction, in a vessel are identified.

Accurate diagnosis of constrictions in vessels, such as the carotid artery, assists medical treatment planning. Three-dimensional ultrasound images of the carotid are rendered from blood flow information. The user subjectively examines the geometry of the rendering for any constriction. This examination typically requires skill and experience to distinguish an actual stenosis from an image artifact or natural vessel variations.

BRIEF SUMMARY

The present invention is defined by the following claims, and nothing in this section should be taken as a limitation on those claims. By way of introduction, the preferred embodiment described below includes a method and system for automated flow analysis. Multiple cross-sectional areas along a vessel are determined automatically. A processor locates an abnormality as a function of the multiple cross-sectional areas, such as identifying a cross-sectional area that is a threshold amount less than an average cross-sectional area. The abnormal area is highlighted on the display to assist with medical diagnosis. Other methods of user notification (e.g., audible warning) are provided.

For the carotid artery, the interior and exterior branches are labeled to assist medical diagnosis. The two branches are automatically identified. The branch associated with additional small branches is identified as the exterior carotid.

Further aspects and advantages of the invention are discussed below in conjunction with the preferred embodiments.

DETAILED DESCRIPTION OF THE PREFERRED EMBODIMENTS

Constrictions or stenosis in a vessel are identified automatically with an ultrasound system. Multiple cross-sectional areas along a vessel are determined by the system. A processor locates an abnormality as a function of the multiple cross-sectional areas, such as identifying a region associated with a cross-sectional area that is a threshold amount less than an average cross-sectional area. The abnormal area is indicated on the display to assist with medical diagnosis.

For the carotid artery, the interior and exterior branches are labeled. The two branches are automatically identified. The branch associated with additional small branches is identified as the exterior carotid.

I. System

Various ultrasound systems are capable of calculating cross-sectional areas or identifying branches and generating a responsive image. For example, a Sequoia®, Aspen™ or 128XP® ultrasound system manufactured by Acuson Corporation may be used. Other ultrasound systems, such as systems provided by other manufacturers or remote workstations, may be used.

Figure 1:
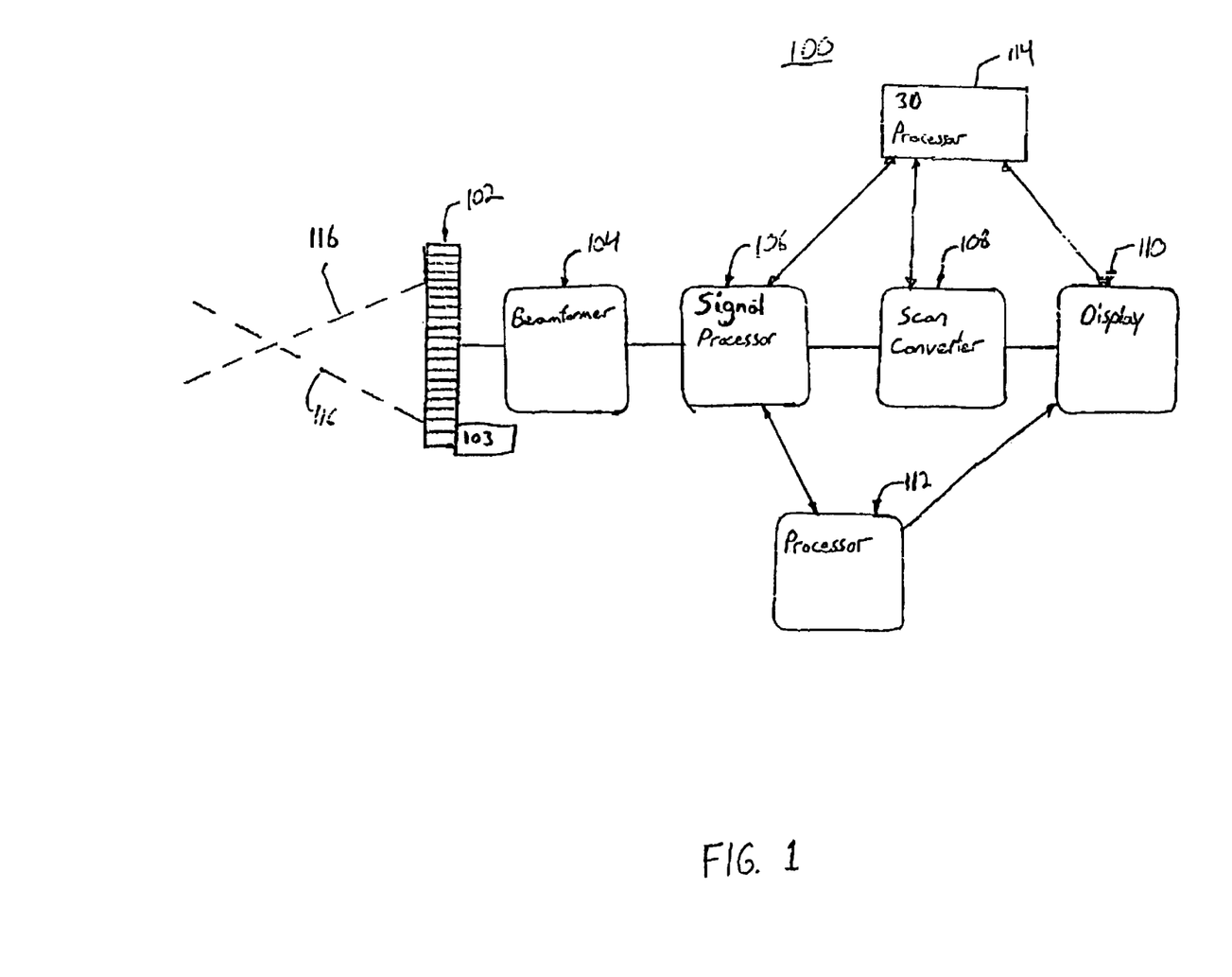
FIG. 1 is a block diagram of one embodiment of a medical diagnostic ultrasound system for automatically assisting with medical diagnosis.

FIG. 1 shows one embodiment of an ultrasound system for assisting medical diagnosis at 100. The system 100 includes a data path comprising a transducer 102, a beamformer 104, a signal processor (estimator) 106, a scan converter 108 and a display device 110. A processor 112 connects to the data path, such as connecting at least to the signal processor 106. A three-dimensional image processor 114 also connects to the data path, such as connecting with one or more of the signal processor 106, the scan converter 108 and the display device 110. In alternative embodiments, the three-dimensional image processor 114 is within the data path, such as being part of the signal processor 106 or scan converter 108, between the signal processor 106 and scan converter 108, or between the scan converter 108 and the display device 110.

The transducer 102 is any of various transducers, such as a linear or curved linear array of piezoelectric elements. In one embodiment, a multi-dimensional transducer is used. For example, multiple image registration or 1.5 or 2 dimensional transducers are used. These transducers include elements arrayed substantially on a flat or curved plane (i.e. arrayed in two dimensions). For a description of multiple image registration transducers, see U.S. Pat. No. 6,014,473, the disclosure of which is incorporated herein by reference. One multiple image registration transducer embodiment includes elements in a plane arrayed in an I pattern. Three scan planes associated with the I pattern may be generated. For T or + beam pattern transducers, two scan planes associated with the T and + patterns, respectively, may be generated. Transducers with other element patterns may be used. For 1.5 or 2 dimensional transducers, any of the various scan plane formats or patterns may be generated.

In one embodiment, the transducer 102 is connected with a catheter or endoscope for insertion into a patient. For example, the transducer 102 is provided on an AcuNav™ Acuson ultrasound imaging catheter or the catheter described in U.S. Pat. No. 5,876,345, the disclosure of which is incorporated herein by reference. Other catheter and transducer devices may be used. As another example, the transducer 102 is provided on one of the endoscopes described in U.S. Pat. Nos. 5,771,896 or 6,045,508 (application Ser. No. 08/807,384, filed Feb. 27, 1998), the disclosures of which are incorporated herein by reference. Other endoscope and transducer devices may be used. In alternative embodiments, the transducer 102 comprises a hand held or mounted transducer for use external to the patient.

The beamformer 104 is constructed as known in the art. The beamformer 104 may comprise separate transmit and receive beamformers. The beamformer 104 produces excitation signals for each or a subset (i.e. a sub-aperture) of the elements of the transducer 102. The excitation signals are processed, such as by applying a relative delay and/or amplitude, to focus ultrasonic waveforms along one or more scan lines 116. The scan lines 116 may be at any of various angles relative to the transducer 102 and originate at various locations along the transducer 102. The plane defined by two or more scan lines or any linear combination of transducer elements comprises a scan plane.

The acoustic waveforms are reflected off of structures within a body, including moving fluid or contrast agents within an enclosed structure, as echoes. Contrast agents may be injected to improve diagnostic accuracy. For example, any of the commercially available agents, such as Optison™, are injected. Contrast agents are generally injected via an aqueous suspension into a vein.

The echoes are detected by the elements of transducer 102 and provided as voltage signals to the beamformer 104. The beamformer 104 sums the voltage signals and outputs ultrasound data representative of structures along the one or more scan lines.

In one embodiment, the beamformer 104 includes a filter for isolating information in a desired frequency band. For example, a bandpass filter, a highpass filter, a lowpass or combinations thereof selectively pass one or both of data at the transmit fundamental frequency band or data at a harmonic of the fundamental frequency band. As another example, a demodulator and a filter are provided to isolate information at a desired frequency band. The signal processor (estimator) 106 comprises a construction known in the art, such as a Doppler digital signal processor or filtering device for providing Doppler estimates from the representative ultrasound data. The signal processor 106 may also include a parallel B-mode processor or spectral Doppler processor. A clutter filter may also be included. The signal processor 106 estimates the Doppler velocity, energy, and/or variance for each of various points or ranges along each scan line. The estimates and any B-mode information may be stored in a memory, such as a CINE™ or image video loop memory.

The estimates, such as Doppler velocity, and/or any B-mode information representing areas in the scan plane or along a scan line are provided to the scan converter 108. The scan converter 108 is a processor or dedicated hardware for formatting the estimates into a Cartesian coordinate system for display.

The display device 110 comprises a monitor, such as a color monitor, flat panel display, television or other device for displaying an image. For two-dimensional imaging, the scan converted ultrasound data representing the scan plane is displayed on, the display device 110 as a B-mode intensity, Doppler velocity, Doppler energy, or Doppler variance image. Images that are a combination of two or more of these types of data may also be generated.

The processor 112 is a digital signal processor or multi-purpose processor for determining cross-sectional areas from the Doppler velocity estimates or other data or for identifying branches. Alternatively, other hardware, such as an accumulator, summer and buffer, may be used. The processor 112 obtains information, such as Doppler velocities, Doppler energies, Doppler variances, Doppler spectrum parameters, orientation information corresponding to the various scan lines and/or other information for calculating cross-sectional area and generating a image of the vessel or for labeling branches as discussed below.

The processor 112 may also provide control instructions to various components of the system 100. For example, the processor 112 controls the beamformer 104 to generate acoustic waveforms and scan formats and/or controls generating of a three-dimensional representation by the three-dimensional image processor 114. Alternatively, a separate processor provides control of the system 100.

The processor 112 or another processor may also coordinate user input. The user designates a region of interest on a displayed ultrasound image. For example, the region of interest corresponds to pixels associated with the enclosed structure for determination of cross-sectional areas and abnormalities. Alternatively, the region of interest is identified by the system 100 by applying one or more thresholds to the Doppler estimates or B-mode information. The identified regions, regardless of the process of identification, are stored in the processor 112, another processor or a memory separate from the processor 112. Alternatively, the user configures the system 100 to scan only the region of interest.

The processor 112 interacts with the three-dimensional image processor 114 to generate a three-dimensional representation that indicates constrictions. The three-dimensional image processor 114 comprises a remote computer. For example, 3D image processor 114 comprises a remote workstation, such as the AEGIS workstation of Acuson Corporation, or a remote personal computer. Alternatively, an on-board computer is used, such as the processor 112 or another processor. For example, see U.S. Pat. No. 6,159,150 (U.S. Ser. No. 09/196,207, filed Nov. 20, 1998), the disclosure of which is incorporated herein by reference, which discloses integrating a Perspective™ computer within an ultrasound system, such as providing interface cables (e.g. 10/100 BaseT Ethernet connection) between the computer and the processor(s) of the ultrasound system, both contained in the same housing.

For 3D imaging, a plurality of scans of the vessel are performed. The representation is rendered from data from different scan planes by the three-dimensional image processor 114. The data used comprises data output by the signal processor 106 or the scan converter 108, including Doppler velocity, Doppler energy, Doppler variance, B-mode and combinations thereof.

In one embodiment, the three-dimensional image processor 114 and the system 100 comprise the system described in U.S. Pat. No. 5,928,151, the disclosure of which is incorporated herein by reference. The system 100 operates as described in the above referenced '151 patent for rendering an image using data corresponding to harmonic or fundamental frequencies.

To render a three-dimensional representation, the scan planes for the data are aligned. Many approaches can be taken in aligning the image data frames to provide the desired three-dimensional reconstruction of the data. For example, mechanical or electrical systems determine a position of the transducer 102 relative to the patient for each scan plane (e.g. absolute position sensors as represented by optional sensor 103). This positioning device may be a magnetic sensor, such as those available from Ascension Technology, Burlington, Vt. Alternatively, the position of the scan planes may be assumed, entered manually or determined electronically from a 2D or 1.5D transducer array. In another alternative, the data may be used to determine the position of the scan plane, such as described in U.S. Pat. No. 6,014,473. Alternatively, frame location may be estimated as described by Schwartz in U.S. Pat. No. 5,474,073.

For reconstruction, the 3D image processor 114 uses the image data frames and the position information to generate information for the three dimensional representation of a volume. Information from the two-dimensional image data frames is converted to a 3D grid, such as a regularly (equal) spaced volume grid. Successive image data frames are inserted into their appropriate XYZ locations of the 3D volume as a function of the positional information.

Once all frames have been inserted, intermediate points are calculated using three-dimensional interpolation techniques relying on the eight or other number of closest known data points. For example, data samples in the 3D grid are linearly interpolated from neighboring data samples, such as 4 or 8 samples. Other interpolation techniques may be used, such as spline fitting.

Instead of scan planes, spaced line data, such as associated with an ultrasound scan line, is used to interpolate to the 3D grid. These data samples are not yet interpolated to the arbitrary two-dimensional planes by scan conversion. Other approaches to 3D reconstruction may be used, such as a nearest neighbor search.

The 3D image processor 114 uses software to construct the 3D representation based on the input information discussed above. Various commercially available software and fixtures are available for 3D reconstruction. Alternatively, the software for reconstruction of the 3D representation is written specifically for the system 100 described above. The representation is displayed on the display 110.

Various visualization software, such as Fortner Research LLC's T3D, and techniques may be used to present the 3D image or reconstruction on the two-dimensional display. Cross sections can be taken in various planes, including a wide variety of planes selected by the user that do not correspond to the scan planes of the image data. The selected planes are interpolated from the 3D grid data samples. For 3D imaging, the 3D representation on the display 38 may be rotated, zoomed and viewed in perspective as is well known in the art.

Various techniques for 3D imaging are possible, such as surface renderings and volume rendering displays. Volume rendering techniques comprise alpha bending, maximum intensity projection or minimum intensity projection. As an alternative to the surface rendering discussed above, the polygon mesh is derived by applying border detection to each image plane (two-dimensional representation). A polygon mesh is formed by logically linking the detected borders.

The processor 112, the three-dimensional processor 114, the signal processor 106 or another processor automatically analyze the ultrasound data to locate an abnormality or label a branch. Using a memory associated with the processor, such as a hard drive, RAM or other memory, the data for determining cross-sectional information is stored. Alternatively, a separate memory structure that is independent of the processors is used. The stored data is used to locate the abnormality or degree of stenosis.

II. Automated Flow Analysis

The system 100 automatically locates and indicates abnormalities in a vessel. The user may indicate a region of interest and/or direction of flow for this analysis. The system 100 automatically determines the locations of abnormalities in response to the user information and ultrasound data.

Figure 2:
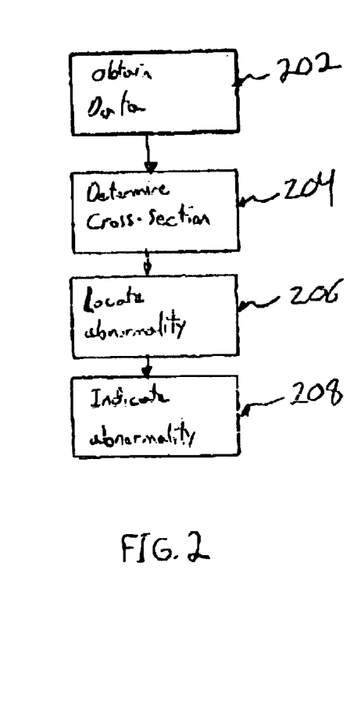
FIG. 2 is a flow chart representing one embodiment for automatically indicating an abnormality in a vessel.

FIG. 2 shows a flow chart of one embodiment for automated flow analysis. In act 202, ultrasound data is obtained. Cross-sections of a vessel are determined from the ultrasound data in act 204. In act 206, one or more abnormalities are located as a function of the cross-sectional information. In act 208, the abnormality is indicated to the user.

For act 202, two or more sets of ultrasound data are obtained. The ultrasound data obtained is in one of various formats. For example, polar or Cartesian coordinate data is obtained. The two sets correspond to different scan planes or regions of the target. The regions overlap or are independent of each other. The regions correspond to a scanned area or a non-scanned area. For a non-scanned area, the ultrasound data is interpolated or extrapolated from other ultrasound data. For example, one or more of the sets of ultrasound data is obtained from a data set representing three-dimensions. Alternatively, one or more of the sets of ultrasound data is associated with two-dimensional scanning. For example, a plurality of sets of ultrasound data corresponds to two-dimensional scans of different regions of the target.

The ultrasound data is obtained using the system 100. For example, a linear transducer is slid along an elevational dimension to obtain the plurality of ultrasound data sets for imaging the carotid artery. The relative position of each scan or the transducer for each scan may also be obtained. As described above, Doppler estimates, such as Doppler energy, velocity or variance estimates, are obtained in response to each scan. Alternatively, B-mode or data that is a combination of Doppler estimates and/or B-mode data is obtained.

In one embodiment, one type of data is segmented from another type of data where a combination of types of data is obtained. For example, Doppler energy or velocity data is segmented from B-mode data, and the Doppler energy or velocity data is used to automatically analyze the vessel.

In one embodiment, the ultrasound data is processed to remove artifact, speckle or other noise related signals. For example, Doppler data is passed through a clutter filter to remove color flash artifacts. The processing is performed prior to or after obtaining the data for flow analysis.

The ultrasound data represents a vessel in the target. The processing of the ultrasound data to locate an abnormality may be performed without regard to any variation of flow. However, the flow and associated Doppler information from a vessel may be cyclical as a function of time. For cyclical flow, such as in the carotid, the ultrasound data used for locating an abnormality is phased to the cycle. For a cardiac cycle, an EKG trigger device triggers each scan so that data is acquired from a same phase of the cardiac cycle. As an alternative to the EKG device, data acquisition is phased in response to a cycle determined from Doppler data, such as phasing in response to a Doppler velocity cycle. For example, U.S. Pat. No. 6,180,320 (Ser. No. 09/370,060, filed Aug. 6, 1999) discloses determining a phase of the cardiac cycle from color Doppler values extracted from a dual mode image.

In act 204, two or more cross-sections of a vessel represented by the sets of ultrasound data are determined. The vessel is identified from the ultrasound data. The end points or section of the vessel for analysis are determined. For example, the end points are determined as being at the edges of the three-dimensional region represented by the ultrasound data (i.e., the extent of the three-dimensional scan). As another example, the end points of the vessel for analysis are selected by the user. A three-dimensional representation is displayed, and the user indicates the end points. Ultrasound data associated with portions of the vessel beyond the end points is clipped or not used.

Figure 3:
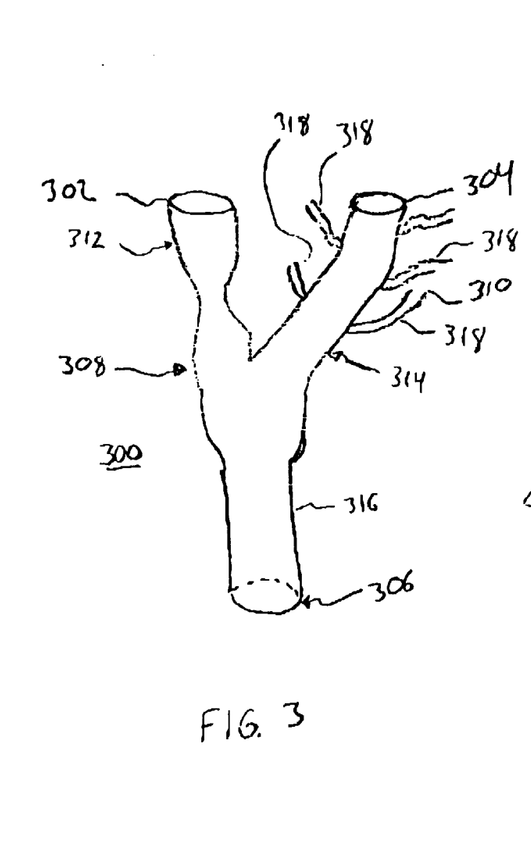
FIG. 3 is a graphical representation of one embodiment of a vessel.

FIG. 3 shows a representation of the carotid artery 300 in one embodiment. The end points 302, 304 and 306 are determined for each branch of the carotid artery 300. For example, the scans are associated with an approximately 4 cm section of the carotid artery (e.g. from the end point 306 to the bifurcation endpoints 302, 304 is about 4 cm). In this example, 2 cm of the carotid artery 300 for analysis is above a bifurcation 308 (carotid bulb) and 2 cm of the carotid artery 300 for analysis is below the bifurcation. Other spatial orientations, ranges and/or vessels may be used.

A central axis, within the vessel between the end points 302, 304, 306 is calculated. The ultrasound data representing two-dimensional regions between the end points is segmented into sets of ultrasound data. Ultrasound data representing planes perpendicular to a line between the end points 302, 304 and 306 is segmented. Ultrasound data associated with other planes or two-dimensional regions may be used, such as associated with scan planes that are or are not perpendicular to the line between end points. Preferably, the ultrasound data sets are associated with substantially evenly spaced two-dimensional regions about perpendicular to the direction of flow or axis of the vessel.

Figure 4:
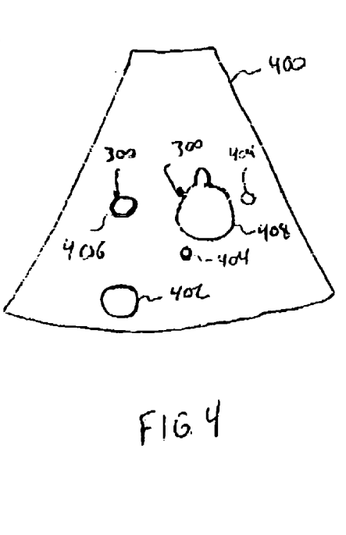
FIG. 4 is a graphical representation of one embodiment of an ultrasound image of a cross-section of the vessel of FIG. 3.

For each set of ultrasound data, a cross-sectional center of gravity for the vessel 300 is determined. The cross-section of the vessel 300 is selected automatically as a function of a threshold or in response to user entry of the cross-section region. The threshold or user input isolates data of interest, such as data associated with an amount of flow indicative of a vessel. FIG. 4 shows a cross-sectional scan plane 400 representing a plane along line 310 of FIG. 3. The vessels 300 are represented by ultrasound data, such as Doppler energy data, indicative of flow.

The ultrasound data associated with each of the vessels is separated from ultrasound data associated with other vessels. In FIG. 4, the vessel 300 has a large area in a cross-sectional image while smaller vessels 404 have smaller areas. The vessel 300 is separated from the smaller vessels 404 by using an erosion and dilation method such as the one described in pages 92–97, "Computer Vision and Image Processing—a practical approach using CVIPtools", Scott E. Umbaugh, Prentice Hall PTR, Upper Saddle River, N.J. 07458. Furthermore, three dimensional connectivity of vessels is also used to segment the carotid artery from the background vessels. See U.S. Pat. No. 6,22217,520 (Ser. No. 09/204,662, filed Dec. 2, 1998), the disclosure of which is incorporated herein by reference, for methods of extraction of an object of interest. Ultrasound data representing areas of contiguous flow represent an individual vessel. Alternatively, ultrasound data representing areas of substantially contiguous flow represent an individual vessel. If a spatial location associated with flow is within 2 to N where N is the number of spatial locations along a single direction, such as N=4, of another spatial location associated with flow, the spatial locations are determined as being for a same vessel. N comprises one of various units of measurement, such as an absolute distance measurement, a number of pixels associated with a display, a number of samples associated with digital receive beamforming or other units.

In alternative embodiments, the above described vessel association process is performed on the ultrasound data set representing three-dimensions (i.e. is performed in three-dimensions). The ultrasound data is then separated into sets for determination of the center axis of the vessels.

In one embodiment, ultrasound data associated with one or more vessels is automatically removed from the flow analysis. For example, scans of the carotid artery often include the jugular vein 402. To isolate the ultrasound data associated with the carotid artery from the ultrasound data associated with the jugular vein, the system 100 automatically analyzes the direction of flow or hemodynamics of the identified vessels. The direction of flow in the carotid artery is opposite to the direction of flow in the jugular vein. The sign of Doppler velocity estimates indicates the direction of flow. Based on user input (e.g. selection of a flow direction or vessel) or a known orientation of the transducer 102, the system 100 automatically identifies the carotid artery 300 and jugular vein 402 as a function of the sign. Alternatively, an assigned color for display based on Doppler velocity estimates is used to distinguish vessels (e.g. red for one direction and blue for the opposite direction). In yet another alternative, a structural feature is used to identify one vessel from another.

Other hemodynamic characteristics may be used to distinguish vessels, such as steady flow verses pulsitile flow, different flow cycles, speed of flow, volume of flow or area of flow. For example, ultrasound data associated with small vessel cross-sectional areas is removed. A threshold area is used to isolate larger vessels. Alternatively or additionally, the vessels are isolated as a function of relative size. Ultrasound data for all but the two largest vessel cross-sections is removed. Any of the various types of ultrasound data, such as Doppler velocity or energy data, may be used for determining hemodynamic characteristics.

The center of the isolated vessel 300 is determined. The center corresponds to a center of a cross-section of the isolated vessel 300. For example, a center of gravity calculation is performed for each vessel 300. The center of gravity is the point at which the first moment of the area is zero in any direction. In one embodiment, the pixel areas are weighted as a function of the associated ultrasound data, such as Doppler energy data, to determine a center of flow.

The center of the vessel 300 is determined for each set of ultrasound data. The center points are joined from one end point to another to determine the center of the vessel 300 in three-dimensions. The centers for contiguous areas of flow in each dimensional are joined to isolate one vessel or vessel branch from another.

In one embodiment, the medial axis of a three-dimensional object is determined using a hybrid thinning/distance-mapping technique. A threshold is applied to the ultrasound data, and each voxel is assigned a 1 or 0 as a function of a threshold. Surface voxels (e.g. any voxel with a 1 value adjacent to a voxel with a 0 value) are identified. The user selects end points of the vessel or vessel branch. An initial path between the selected end points is found by distance-mapping along the surface. For example, the surface voxels closest to the selected end points are identified (e.g. the surface voxel A' closest to the end point A is identified). The voxels along a line A–A' from each end point to the selected closest surface voxels are also added to the identified surface voxels. Starting from one of the end points, distance values are assigned to each surface voxel along the line A–A' as a function of the distance from the end point, and then distance values along the rest of the surface values are assigned as a function of the point A' and the distance value assigned to A'. A shortest path along the vessel is identified as a function of the distance map. The surface is reduced or thinned as a function of the shortest path. After each morphological thinning step, a new path is found by distance mapping along the new surface using the old path between disconnected components. The medial axis path is left after thinning has eroded away the entire object. For example, D. S. Paik, C. F. Beaulieu, R. B. Jeffrey, G. D. Rubin, S. Napel, "Automated flight path planning for virtual endoscopy," Medical Physics, May, 1998; 25(5): 629–637.

In another embodiment, the center of the vessel or vessel branches is identified as disclosed in (Ser. No. 09/607020, filed herewith. Data associated with flow is weighted. A local gradient of the weights is determined. A magnitude of the gradients determines or amount of reduction of the vessel boundary by dilation (e.g., an inversely proportional function). The center is identified by this dilation.

Where the vessel 300 bifurcates, the centers of the two branches join. The center axis of each branch is projected into the trunk of the vessel. The center axis of the trunk is determined from a location where the two projections are closest and at locations further away from the vessel bifurcation. Other functions may be used to determine the center of the vessel 300 at bifurcations. In alternative embodiments, the user designates the center of the vessel 300. In yet another alternative embodiment, the center of the vessel 300 is assumed to be a straight or other line between the end points.

In act 204 (FIG. 2), the cross-sectional area of the vessel 300 is determined at various locations along the vessel 300. At each location, a plane is defined that is perpendicular to the central axis of the vessel at that location. The cross-product of two vectors lying on the plane is in the same direction or has the same slope as the central axis of the vessel at that location.

For the bifurcation, the plane is perpendicular to one or the other branches. A plane that is as perpendicular as possible to both branches may be used. The common area may be divided between the two branches and both branches analyzed separately. For example, the automatic division of cross-sectional area at a bifurcation disclosed in (Ser. No. 09/607020, filed herewith for a Medical Diagnostic Ultrasound System and Method for Imaging a Vessel Bifurcation, the disclosure of which is incorporated herein by reference, is used. By dividing the cross-sectional area at a bifurcation between two branches, the center axis of the vessel or cross-sectional areas of the vessels are more accurately determined. For example, a ratio of an integral of the energy or velocity of the flow in each branch is used to assign the common area of the bifurcation to each branch. As another example, the intersection of two places perpendicular to the branch centers in the common area of a bifurcation divides the area attributable to each branch.

The cross-sectional area is calculated from ultrasound data representing the vessel 300 in the plane. For example, the cross-sectional area is calculated from ultrasound data representing a contiguous area where the ultrasound data is above a threshold. In alternative embodiments, the cross-sectional area is represented by the number of spatial locations (e.g. pixels or sample regions) within a contiguous area defined as the vessel 300. The cross-sectional area is determined separately for each vessel 300 or vessel branch.

In act 206 (FIG. 2), any abnormality is automatically located as a function of the cross-sectional areas. Where the vessel 300 includes a bifurcation 308, a branch for analysis is selected. The trunk and the branch of the vessel 300 are analyzed as one vessel or separately. The other branch of the bifurcated vessel may also be analyzed separately or with information relating to the trunk.

For the vessel being analyzed, the cross-sectional area at spaced locations along the vessel 300 is compared to at least one other cross-sectional area along the vessel 300. For example, an average cross-sectional area is determined. An abnormality is located at any location where the cross-sectional area of the location is smaller than the average by a threshold amount. For example, a location associated with a cross-sectional area that is 50% or less of the average is the location of an abnormality. Other threshold values may be used, including dynamic, preset or user selected values. In one embodiment, the threshold is determined by analyzing the data from different groups of patients. Groups may be based on some physical or physiological attribute, such as age, weight, cholesterol levels and other risk factors.

As an alternative to determining an average cross-sectional area, a weighted average is used. The weights account for one or more of whether the cross-section is associated with a branch or a trunk, a bifurcation bulb, an vessel region subject to external pressure or other non-stenosis factors contributing to a constriction of the vessel. In yet other alternative embodiments, the cross-sectional area at each location is compared to one or more adjacent or spaced cross-sectional areas.

Alternatively, if the cross-sectional area is significantly larger than normal (e.g. a threshold) or an average, an image artifact may be indicated. In this situation, the user is prompted re-scan the target.

In some situations, the length of a stenosis or constriction is measured. The abnormality exists along a length of the vessel. Where multiple abnormalities are located in a contiguous or substantially contiguous section (e.g. every second or third cross-section) of the vessel 300, a single stenosis may be automatically located. The length of the stenosis is determined from the length of the vessel or center axis associated with the abnormality. For example, a single plane or cross-section represents 2 mm. Where one cross-section indicates an abnormality, the stenosis is 2 mm long. Where three contiguous cross-sections indicate an abnormality, the stenosis is 6 mm.

In act 208 (FIG. 2), the system 100 automatically indicates the constriction to the user. In one embodiment, a graph representing the cross-sectional area as a function of location along the vessel 300 is generated on the display 110. The graph may be displayed as a function of time showing the dynamic nature of the variation of the area vs. distance over the cardiac cycle. It may also be shown as a 2D surface, two independent axes comprising distance along the vessel and the time, while the third dependent axis comprising the cross sectional area. The abnormality may be further indicated by highlighting (e.g. color or brightness of the graphed line or by positioning a threshold line relative to the graph) sections of the graph associated with the abnormality. The indication and flow analysis may be repeated for multiple branches or vessels at a same or different time.

Alternatively or additionally, the abnormality is indicated to the user on an image representing the vessel 300. An image is generated as discussed above. The image comprises one or both of a two-dimensional image or a three-dimensional representation. The image is generated from the same or different ultrasound data as used for locating the abnormality. For example, a different type of data is used, such as B-mode data. As another example, data from a different scan is used, such as data obtained before or after the data used to locate the constriction.

The image represents the vessel 300. Regions associated with abnormalities are highlighted on the image. For example, pixels representing a region of the vessel corresponding an abnormality are changed in intensity or hue. Additionally or alternatively, an arrow, line, or other indicator is displayed adjacent to the region associated with the abnormality.

In one embodiment, the system 100 automatically indicates a relative severity of multiple constrictions. The severity is determined as a function of the cross-sectional area, the length of the stenosis, the ultrasound data representing flow within the vessel or combinations thereof. Worse constrictions are indicated with brighter highlighting, by numerical indication, or other labeling. Alternatively, an audible warning, such as a beep or synthetic, computer based speech, may be used to alert the user. Other forms of user notification may also be used.

Numerical information may be provided. For example, the cross-sectional area, ratio of a constriction cross-sectional area to average cross-sectional area, the length of the stenosis, a diameter, a radius or other value is displayed for one or more abnormalities.

Since fluids in many vessels change as a function of time in response to the cardiac cycle, images and abnormality determinations associated with the vessel for each of a plurality of phases of the cardiac cycle may be obtained. A chamber or other object may be visualized as described above, such as a surface rendering, as a function of time. For example, the 3D representation is displayed as a series of images within a heart cycle. This dynamic 3D representation indicates changes in shape and volume over time. Any abnormalities are determined for each series of images.

In an alternate embodiment, just the central axis of the vessel tree is displayed as a connected set of three-dimensional lines and curves. Properties such as cross sectional area or severity of stenoses, are also displayed in the above display as a color-coded segments of three-dimensional lines and curves. The display may vary over time as a function of the cardiac cycle, resulting in a four dimensional display of a dynamic color-coded skeleton of the vascular tree.

Figure 5:
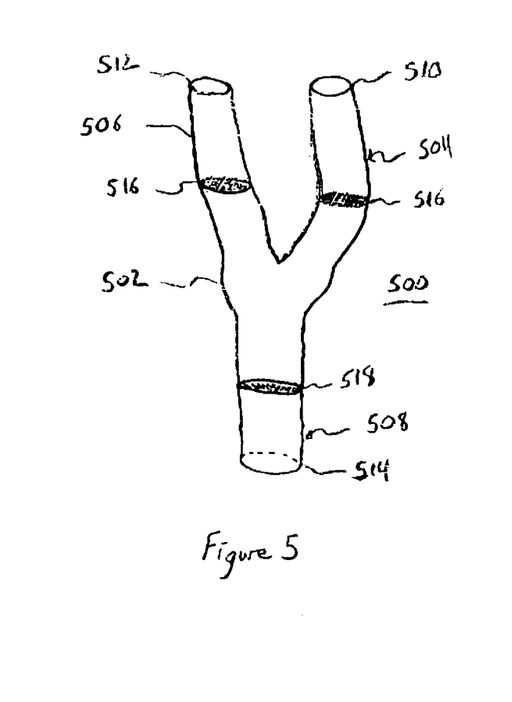
FIG. 5 is a graphical representation of one embodiment of a vessel.

As an alternative or in addition to analyzing each branch separately as discussed above, two or more branches are automatically analyzed together. FIG. 5 shows a vessel 500 with a bifurcation 502. Each branch 504, 506 and the trunk 508 is associated with an end point 510, 512, 514, respectively.

Two different cross-sectional areas are calculated by the system 100 for a plurality of locations spaced along the vessel between the end points 510, 512 and to 514. First, a total cross-sectional area is determined for multiple locations along the entire length of the vessel 500. The total cross-sectional area for locations along the trunk 508 is the cross-sectional area 518 of the trunk. The total cross-sectional area for locations between the bifurcation 502 and the branch end points 510, 512 is the sum of the cross-section 516 for each branch 504, 506.

Second, the cross-section 516 of one branch 504 is determined for multiple locations between the bifurcation 502 and the branch end point 510. The multiple locations comprise the same locations used for calculating the total cross-sectional area. Where additional bifurcation exist, the cross-section of the one branch 504 is determined as one of the additional branches.

The cross-sectional areas are calculated for areas perpendicular to an angle of flow or the center axis of the vessel 500. For example, the point along each branch center axis a same distance away from the trunk end point 514 is determined. The cross-sectional areas 516 used are calculated for a plane perpendicular to the center axis of the branch 504 or 506 that includes the point. Alternatively, a plane through all or a sub-set of points in multiple branches is determined. The cross-section for each branch within that plane is calculated.

Abnormalities are determined by examining the two cross-sectional areas discussed above and/or a difference of the cross-sectional areas. FIGS. 6A–6D are graphic representations of these three cross-sectional areas as a function of distance, S, along the vessel 500 where $S_b$ represents the location of the bifurcation 502. The solid line, $A_T$, represents the total cross-sectional area. The dashed line, $A_B$, represents the cross-sectional area of the branch. The dot-dashed line, $A_T - A_B$, represents the difference.

Figure 6A:
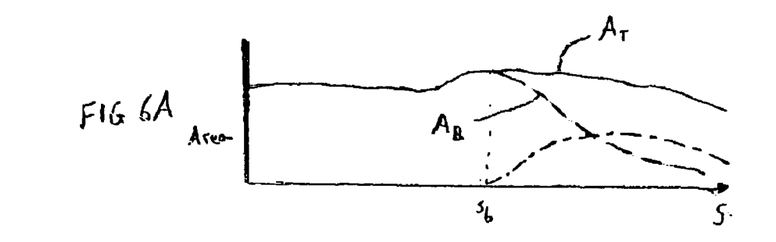
FIGS. 6A–6D are various embodiments of graphs of cross-sectional area as a function of location.
Figure 6B:
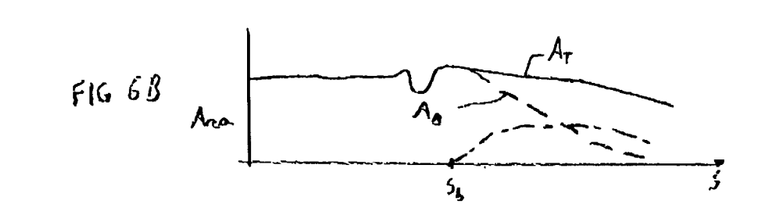
Figure 6C:
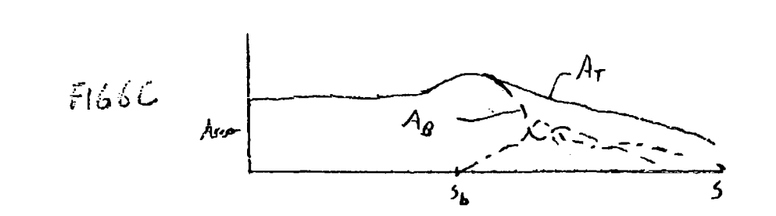
Figure 6D:
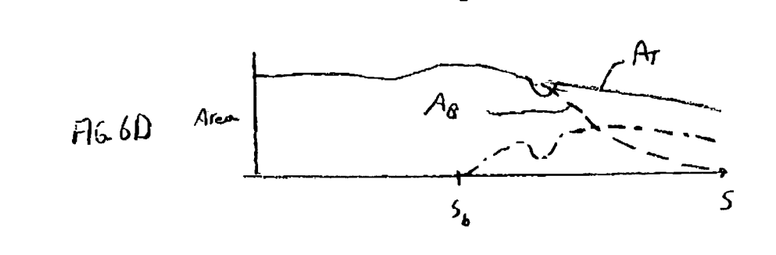

FIG. 6A represents the vessel 500 without abnormalities. FIG. 6B shows the vessel 500 with a constriction in the trunk 508. A dip in the total cross-sectional area shows the location and extent of the constriction. FIG. 6C shows the vessel 500 with a constriction in the branch 504 used for the branch cross-sectional area. A dip in the branch cross-sectional area and a bump in the difference shows the location and extent of the constriction. FIG. 6D shows the vessel 500 with a constriction in the branch 506 not used for the branch cross-sectional area. A dip in the total cross-sectional area and the difference, but not in the branch used for the cross-sectional area shows the location and extent of the constriction.

In one embodiment, the location and extent of the constriction is determined without calculating the difference. The cross-sections of additional branches may also be independently determined.

To indicate the location of the abnormality to the user, graphs as shown in FIGS. 6A–6D are generated on the display. Other indications may be used, such as the indications discussed above. Also as discussed above, a comparison of each cross-sectional area, such as the total, different or a branch cross-sectional area, to other cross-sectional area measurements may be used. For example, an average total cross-sectional area is calculated and compared to each separate total cross-sectional area to locate an abnormality.

III. Further Automation

In one embodiment, the system 100 determines and labels the separate branches of the carotid artery. At the bifurcation 308, the interior and exterior branches 312 and 314 extend from the trunk 316 of the vessel 300. The interior branch 312 provides blood to the brain, and the exterior branch 314 provides blood to the face. Since obstructions of flow to the brain may be more serious than obstructions to the face, the system 100 assists in focusing examination of the proper vessel and/or assists in determining the urgency or type of treatment necessary. By automated determination, radiologists may more quickly focus analysis on abnormalities, rather than vessel identification. Branch determination techniques may be applied to other vessels with bifurcations.

There are several characteristics that can be used to determine the internal from the external branch of the carotid:

(1) The internal carotid has few or no branches. The external carotid has branches that may or may not be visible based on (a) the extent of the external branch scanned and (2) the size of the flow within the branch.

(2) The internal branch tends to be more medially placed and the external tends to be more laterally placed. For imaging, with an external transducer array, the internal branch may appear in the image to be closer to the transducer.

(3) Because the brain vasculature provide low-resistance to flow, flow through the internal carotid artery has little diastolic component. On the other hand, flow in the external carotid may contain a significant diastolic component. The characteristic of flow are compared to each other or a threshold to determine the internal and external carotid.

There are conditions that may make some or all of these determinations difficult. In one embodiment, two or more of the results are used to make the final determination. A weighted sum, where the weights are determined in advance using a "training set" developed through experimentation and human selection is applied. Fuzey logic or other functions may be used.

In one embodiment, at least one cross-section scan that includes both the interior and exterior carotid artery is obtained. For example, FIG. 4 shows one such cross-sectional scan. The cross-sectional scan is obtained from a set of ultrasound data representing three-dimensions or a two-dimensional scan of the region. Preferably, a plurality of cross-section scans are obtained, such as associated with a set of data representing three-dimensions. In one embodiment, the scans are associated with a same phase of the cardiac cycle.

Contiguous vessel areas or volumes are determined as discussed above. For example, the jugular vein 402, the interior and exterior carotid arteries 406 and 408, and a plurality of smaller branches 404 are identified. The flow is continuous through a branch or vessel (i.e. blood in a branch is from the trunk vessel). As also discussed above, ultrasound data for one or more of the identified vessels may be removed, such as removing data associated with the jugular vein 402.

The exterior carotid has a plurality of small branches 318 (FIG. 3), 404 (FIG. 4). The interior carotid has few or no small branches near (e.g., immediately distal) the bifurcation 308. The system 100 identifies the two largest vessels after the bifurcation 308. The largest vessel with the most smaller branches 318, 404 is identified as the exterior carotid 314, 408.

In one embodiment, the carotid trunk 316, exterior carotid 314 and interior carotid 312 are distinguished from smaller branches 318 by iteratively removing ultrasound data representing the surface of each vessel. This process is performed using a data set representing three-dimensions or one or more sets representing two dimensions. Smaller vessels disappear first. Once distinguished, the system 100 tracks the interconnections between vessels, such as determining the joining of axes at bifurcations as discussed above. In alternative embodiments, the user inputs a selection of two vessels likely to be the interior or exterior branches.

In another automatic alternative, the cross-sectional area is used to identify the interior and exterior carotid 312 and 314. The areas defined as continuous include spatial locations associated with flow spaced 2 to N units away from another spatial locations associated with flow. Smaller branches are more likely to be included within the cross-sectional area being examined. The area of the exterior carotid 314 with the additional smaller branches included is more likely to have an apparent larger cross-section, assuming the actual interior and exterior carotid arteries cross-sections are substantially the same size. The interior and exterior carotid arteries 312 and 314 are labeled on the display 110. For example, the interior carotid artery 312 is displayed with a different color, hue or brightness than the exterior carotid. As another example, a label adjacent to or with an arrow or line connecting to the appropriate artery is displayed.

The display may include identification of abnormalities as discussed above. For example, a separate graph of vessel cross-sectional area is provided for and labeled for each of the interior and exterior carotid arteries 312, 314. Given the abnormality information and the vessel identification, the system 100 automatically provides information to assist with proper medical diagnosis.

The ultrasound data used to identify the vessel 300 comprises Doppler velocity, variance or energy estimates, B-mode data or combinations thereof. Where the system 100 is unable to identify a vessel 300, a warning or other indication is provided to the user. Information, such as a numerical value or bar graph, indicating the confidence of the vessel and/or abnormality identification may be provided to the user.

In one embodiment, one or more of the techniques or systems described herein are performed in combination with the stenosis identification techniques and systems disclosed in (Ser. No. 09/606,515, filed on Jun. 29, 2000), for a Medical Diagnostic Ultrasound System and Method for Identifying Constrictions, the disclosure of which is incorporated herein by reference. Constrictions are determined as a function of volume flow measurements along a vessel. The cross-sectional area based identification of abnormalities is used to confirm accurate identification using volume flow measurements, vise versa or as a weighted combination.

As used in this application, the term "vessel" includes any enclosed region or zone in a body that permits fluid flow therein.

While the invention has been described above by reference to various embodiments, it will be understood that many changes and modifications can be made without departing from the scope of the invention. For example, the user may adjust or provide input during one or more of the various automatic acts described above.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound method for automated flow analysis, the method comprising the acts of:
   (a) obtaining first and second data sets corresponding to first and second two dimensional areas of a target, the target including a vessel;
   (b) determining first and second cross-sectional areas of the vessel from the first and second data sets, respectively, with a processor;
   (c) locating an abnormality as a function of the first and second cross-sectional areas with the processor; and
   (d) indicating the abnormality to the user.

2. The method of claim 1 further comprising:
   (e) generating a set of ultrasound data representing a three-dimensional region of the target;
   wherein the first and second data sets are included within the set of ultrasound data representing the three-dimensional region.

3. The method of claim 1 wherein (b) comprises determining the first and second cross-section areas as a function of Doppler data.

4. The method of claim 3 wherein (b) comprises determining the first and second cross-section areas as a function of Doppler energy data.

5. The method of claim 3 wherein (b) comprises determining the first and second cross-section areas as a function of distance along the vessel.

6. The method of claim 1 wherein (d) comprises displaying a graph representing cross-sectional area as a function of distance along the vessel.

7. The method of claim 1 further comprising:
(e) determining an analysis branch as one of two branches in the vessel;
wherein (b) and (c) are performed as a function of the analysis branch.

8. The method of claim 7 wherein (e) comprises:
(e1) identifying first and second branches of the vessel with the processor; and
(e2) selecting one of the first and second branches as a function of a number of small branches connected with the first and second branches.

9. The method of claim 1 further comprising:
(e) excluding data for (b) as a function of a sign of Doppler velocity data.

10. The method of claim 1 further comprising:
(e) excluding data for (b) as a function of hemodynamics.

11. The method of claim 1 wherein (b) comprises determining a branch cross-sectional area of a branch of the vessel and a sum of cross-sectional areas of a plurality of branches and (c) comprises locating the abnormality in the branch as a function of the branch cross-sectional area and sum.

12. The method of claim 1 further comprising:
(e) triggering (a) in response to a cardiac cycle.

13. The method of claim 1 wherein (d) comprises generating an audible output.

14. A medical diagnostic ultrasound system for automated flow analysis, the system comprising:
a memory operable to store first and second data sets corresponding to first and second two dimensional areas of the target, the target including a vessel;
a processor operable to determine first and second cross-sectional areas of the vessel from the first and second data sets, respectively; and
an output device operable to indicate an abnormality as a function of the first and second cross-sectional areas.

15. The system of claim 14 further comprising a three-dimensional data processor for generating a set of ultrasound data representing a three-dimensional region of the target;
wherein the first and second data sets are included within the set of ultrasound data representing the three-dimensional region.

16. The system of claim 14 wherein the first and second data sets comprise Doppler data.

17. The system of claim 16 wherein the first and second data sets comprise Doppler energy data.

18. The system of claim 14 wherein the output device comprises a display that displays a graph representing cross-sectional area as a function of distance along the vessel.

19. The system of claim 14 wherein the processor determines an analysis branch as one of two branches in the vessel, and wherein the cross-sectional areas are determined as a function of the analysis branch.

20. The system of claim 14 wherein data from the first and second data sets is excluded as a function of a sign of Doppler velocity data.

21. The system of claim 14 wherein data from the first and second data sets is excluded as a function of hemodynamics.

22. The system of claim 14 further comprising a transducer having at least two orthogonal arrays operatively connected with the memory.

23. A medical diagnostic ultrasound method for automated flow analysis of a vessel, the method comprising the acts of:
(a) automatically determining first and second cross-sectional areas of the vessel from first and second ultrasound data sets, respectively; and
(b) indicating an abnormality as a function of the first and second cross-sectional areas.

24. The method of claim 23 further comprising:
(c) obtaining the first and second ultrasound data sets from a set of ultrasound data representing a three-dimensional region of the target.

25. The method of claim 23 wherein (a) comprises determining the first and second cross-section areas as a function of Doppler data.

26. The method of claim 23 wherein (b) comprises displaying a graph representing cross-sectional area as a function of distance along the vessel.

27. The method of claim 23 further comprising:
(c) automatically determining an analysis branch as one of two branches in the vessel;
wherein (a) and (b) are performed as a function of the analysis branch.

28. The method of claim 23 further comprising:
(c) excluding data for (a) as a function of a sign of Doppler velocity data.

29. The method of claim 23 further comprising:
(c) excluding data for (a) as a function of hemodynamics.

30. The method of claim 23 wherein (b) comprises generating an audible output.

31. A medical diagnostic ultrasound method for automated carotid vessel analysis, the method comprising the acts of:
(a) identifying first and second branches of the carotid vessel with a processor;
(b) selecting one of the first and second branches as a function of the number of small branches connected with the first and second branches; and
(c) automatically labeling the selected one of the first and second branches on a display.

32. The method of claim 31 wherein (a) comprises:
(a1) determining contiguous flow regions from ultrasound data representing a three-dimensional region of a target; and
(a2) identifying the first and second branches as a function of the contiguous flow regions.

33. The method of claim 31 wherein (b) comprises selecting the external carotid as the one of the first and second branches associated with the most small branches and selecting the internal carotid as the other of the first and second branches.

* * * * *

UNITED STATES PATENT AND TRADEMARK OFFICE
CERTIFICATE OF CORRECTION

PATENT NO.    : 6,503,202 B1
DATED         : January 7, 2003
INVENTOR(S)   : Hossack et al.

It is certified that error appears in the above-identified patent and that said Letters Patent is hereby corrected as shown below:

<u>Title page,</u>
Item [73], Assignee, after "Acuson Corp., Mountain View, CA" add -- and The Board of Trustees of the Leland Stanford Junior University, Palo Alto, CA, as joint owners --

Signed and Sealed this

Eleventh Day of November, 2003

JAMES E. ROGAN
*Director of the United States Patent and Trademark Office*